United States Patent
Seki et al.

(10) Patent No.: US 6,958,036 B2
(45) Date of Patent: Oct. 25, 2005

(54) ENDOSCOPIC MANUAL CONTROL KNOB, AND A METHOD FOR MANUFACTURING SAME

(75) Inventors: Hidetoshi Seki, Saitama (JP); Kazuhiko Hino, Saitama (JP); Haruo Akiba, Koga (JP)

(73) Assignee: Fujinon Corporation, Saitama (JP)

( * ) Notice: Subject to any disclaimer, the term of this patent is extended or adjusted under 35 U.S.C. 154(b) by 0 days.

(21) Appl. No.: 10/401,612

(22) Filed: Mar. 31, 2003

(65) Prior Publication Data

US 2003/0187328 A1 Oct. 2, 2003

(30) Foreign Application Priority Data

Mar. 29, 2002 (JP) .................................... 2002-093956

(51) Int. Cl.[7] .............................................. A61B 1/00
(52) U.S. Cl. ...................... 600/147; 600/146; 600/122
(58) Field of Search ................................ 600/101, 122, 600/146, 147

(56) References Cited

U.S. PATENT DOCUMENTS

| | | | | |
|---|---|---|---|---|
| 5,507,717 A | * | 4/1996 | Kura et al. | 600/146 |
| 6,656,111 B2 | * | 12/2003 | Fujii et al. | 600/146 |
| 6,673,012 B2 | * | 1/2004 | Fujii et al. | 600/146 |

* cited by examiner

*Primary Examiner*—Beverly M. Flanagan
(74) *Attorney, Agent, or Firm*—Oblon, Spivak, McClelland, Maier & Neustadt, P.C.

(57) ABSTRACT

An endoscopic manual control knob which has a knob body proper in the form of a synthetic resin molding. The knob body is largely composed of a ring-like top plate and a peripheral side wall portion fringed along outer periphery of the top plate. The top plate is provided with an aperture to be fitted on a rotatable shaft, and a number of lever portions projecting radially outward from the outer periphery of the top plate at angularly spaced positions. The knob body has an implant block embedded in each one of the lever portions by insert molding.

10 Claims, 5 Drawing Sheets

ENDOSCOPIC MANUAL CONTROL KNOB, AND A METHOD FOR MANUFACTURING SAME

BACKGROUND OF THE INVENTION

1. Field of the Art

This invention relates to a manual control knob for an endoscope, and more particularly to a manual control knob to be mounted on a manipulating head assembly of an endoscope for angularly bending a fore end portion of an insertion instrument, and a method for manufacturing such endoscopic manual control knob.

2. Prior Art

Endoscopes have been and are widely used in medical purposes. In most cases endoscopes are constructed as shown schematically in FIG. 5, including a manipulating head assembly 1 to be gripped by an operator, an insertion instrument 2 which is extended out on the front side of the manipulating head assembly 1, and a universal cable 3 which is led out on the rear side of the manipulating head assembly 1. Provided at the fore distal end of an elongated flexible body portion 2c of the insertion instrument 2 is a rigid tip end section 2a with an illumination window or windows along with an endoscopic observation window for endoscopic observation purposes. Further, provided between the rigid tip end section 2a and the flexible body portion 2c is an angle section 2b which can be angularly bent by remote control to turn the rigid tip end section 2a into an arbitrary direction. On the other hand, the universal cable 3 is provided to connect the manipulating head assembly 1 at least with a light source.

As well known in the art, the angle section 2b of the endoscopic insertion instrument 2 has a flexible articulate structure which can be bent at least in one direction by remote control. Normally, the angle section 2b is arranged to be bendable in four directions, i.e., in upward, downward, rightward and leftward directions. The angle section 2b is bent in one of these directions by way of an angle manipulation mechanism which is provided on the manipulating head assembly 1 of the endoscope.

Shown in FIG. 6 is an angle manipulation mechanism. As clear therefrom, a support plate 5 is provided internally of the manipulating head assembly 1 to mount thereon a tubular support column 6, which rotatably supports a pair of upper and lower pulleys 7 and 8. Upon rotating one of the two pulleys 7 and 8, say, the pulley 7 about the support column 6, the angle section 2b of the insertion instrument is bent laterally in a rightward or leftward direction. Upon turning the other one of the pulleys 7 and 8, say, the pulley 8 about the support column 6, the angle section is bent vertically in an upward or downward direction. In order to bend the angle section 2b in this manner by remote control, a pair of upper and lower operating wires 9 are connected to the pulley 7, while another pair of right and left operating wires 10 are connected to the other pulley 8.

The pulleys 7 and 8 are connected to hollow inner and outer rotatable shafts 11 and 12, respectively. The pulley 7 which is located on the side of the support plate 5 is connected to the inner rotatable shaft 11. The pulley 8 which is located on the upper side of the pulley 7 is connected to the outer rotatable shaft 12. These rotatable shafts 11 and 12 are provided coaxially with the support column 6, and are led out to the outside of a casing of the manipulating head assembly 1 of the endoscope. Manual control knobs 13 and 14 are connected to outer ends of the rotatable shafts 11 and 12, respectively.

When the insertion instrument 2 is introduced into a body cavity, while gripping the manipulating head assembly 1 at the upper end of the insertion instrument, an operator can manipulate the manual control knobs 13 and 14 of the angle manipulation mechanism 8 to bend the angle section of the insertion instrument in a desired direction. The angle manipulation mechanism 4 is provided with lock means 15 and 16 thereby to lock the knob members 13 and 14 against rotational movements for retaining the angle section 2b in a bent state whenever necessary.

The manual control knob 14 which is adopted for bending the angle section 2b in upward and downward directions is shown more particularly in FIGS. 7 and 8. In these figures, indicated at 20 is a molded knob body proper of the manual control knob 14. Through a link member 21, the knob body 20 is securely fixed to the rotatable shaft 12 by means of a screw 22. The knob body 20 is provided with an aperture 23 in its top plate portion 20a to receive the rotatable shaft 12, and the above-mentioned link member 21 is connected to the top plate portion 20a. A peripheral side wall portion 20b is contiguously provided around outer periphery of the top plate portion 20a. These top plate portion 20a and the peripheral side wall portion 20b are formed integrally by synthetic resin molding. The molded knob body 20 is provided with a plural number of lever portions 24, which are projected radially outward from a plural number of positions (five angularly spaced positions in the particular example shown) around the outer periphery of the knob body 20. For turning the knob body 20, an operator puts his or her fingers on the lever portions 24 and push the lever portions 24 to turn the knob body 20 in a desired direction. For this purpose, finger grip surfaces 24a are provided on outer distal end faces of the lever portions 24. In the following description, the molded knob body 20 is assumed to have the top plate portion 20a on the top side, and the outwardly projected lever portions are regarded as outer peripheral portions of the knob body.

In order to turn the manual control knob 14 (or the other manual control knob 13), while gripping the manipulating head assembly 1 of the endoscope in one hand, an operator can put his or her thumb on one of the finger rest surfaces 24a in outer peripheral portions of the knob body 20 to apply a force in a direction the knob member 14 is to be turned. Accordingly, in order to permit an operator to apply a sufficient operating force easily on the knob member 14, it is desirable for the knob body to have a broad finger grip surface on the lever portions. Namely, the finger grip surface 24a on the lever portion 24 should have not only a sufficient breadth in the circumferential direction but also a sufficient height (in a direction substantially parallel with the longitudinal axis of the rotatable shaft 12).

The top plate portion 20a and the peripheral side wall portion 20b of the knob body 20 are formed integrally together by synthetic resin molding, providing lever portions 24 with finger grip surfaces 24a of a large breadth both in circumferential and axial directions. In case the knob body 20 is molded to have solid lever portions 24, there may arise a problem of shrinkage surface sinking, which often results in sunken spots on the surfaces of molded lever portions 24. Such surface sinking can impair the maneuverability and appearance of the knob members to a considerable degree especially in case sunken spots exist on the surfaces of the lever portions 24. The problem of shrinkage surface sinking has thus far been prevented by reducing the thickness of the top plate portion 20a and side wall portion 20b of the knob body 20 to a minimum necessary thickness which would be allowable in terms of strength, as shown in FIG. 8.

The lever portions of the knob members, especially the finger grip surfaces of the lever portions which are repeatedly touched by the fingers of an operator get contaminated easily. Normally, each time an endoscope is washed clean after use. More particularly, an endoscope is washed by immersing the entire body of the endoscope in a cleaning liquid, including not only the insertion instrument, which has been directly introduced into a body cavity, but also the manipulating head assembly and the universal cable of the endoscope. At this time, the manual control knobs of the angle manipulation mechanism are also washed in the cleaning liquid. However, it is often found difficult to clean back side of the respective lever portions and corner portions between the top plate portion and the side wall portion of the knob member to a satisfactory degree.

In an attempt to overcome the above-mentioned problem or difficulty, it has been known, for example, from Japanese Laid-Open Patent Application H11-47082 to fill cavity on the back side of each lever portion with a back nail member in the form of a block of the same synthetic resin material as the knob body and welded to the latter. Namely, in this case, while reducing the wall thickness of the knob body to a minimum necessary thickness which is free of shrinkage surface sinking in a molding stage, the hollow cavity on the back side of each lever portion of the molded knob body is completely filled and closed with the back nail member.

However, in the case of the prior art knob construction just mentioned, the fabrication process becomes complicated and involves an increased number of steps because of the necessity for a step of molding the back nail members in addition to the molding of knob bodies and a step of welding molded back nail members to the back side of the respective lever portions of the knob body. This naturally results in increases in production cost. Besides, unless the back nail members are thoroughly welded to a knob body, there are possibilities of contaminants still remaining in interstices or clevises at incompletely welding portions even after a careful cleaning or washing operation.

SUMMARY OF THE INVENTION

With the foregoing situations in view, it is an object of the present invention to provide an endoscopic manipulation knob of synthetic resin molding, which is provided with substantially solid lever portions free of sunken surface spots or other irregularities and which can be produced in a facilitated manner.

It is another object of the present invention to provide an endoscopic manipulation knob of synthetic resin molding, which is arranged especially to get rid of unwashed or unclean spots on or in the vicinity of finger grip surfaces of the knob.

In accordance with the present invention, in order to achieve the above-mentioned objectives, there is provided a manual control knob suitable for use on an endoscope for manipulation of an insertion instrument, the manual control knob being of the sort having a knob body of synthetic resin molding largely constituted by a ring-like top plate and a peripheral wall portion of a predetermined width formed integrally along marginal edges of the top plate, an aperture perforated centrally through the top plate, a plural number of lever portions projected radially outward from angularly spaced positions around outer periphery of the top plate, each one of the lever portions being provided with a finger grip surface at an outer distal end, and the aperture of the top plate being fitted on a rotating shaft projected from a manipulating head assembly of the endoscopic insertion instrument, characterized in that: the knob body is constituted by a synthetic resin molding having the top plate and the peripheral side wall portion molded integrally with each other and having implant blocks embedded in the lever portions of the top plate by insertion molding; and cover wall portions are formed integrally with the knob body to enshroud the implant blocks completely on a lower back side of the knob body facing away from the top plate.

In this instance, it is desirable that inner peripheral side walls of the implant blocks be at least partly enshrouded by an enfolding wall portion which is formed integrally with the cover wall portion. The knob body and the implant blocks may be formed of the same synthetic resin material if desired. However, different synthetic resin materials may be employed for these parts to impart different properties. For example, it is important to form the knob body by the use of a synthetic resin material with high resistance to chemicals. On the other hand, the implant blocks can be formed either by the use of the same synthetic resin material as the knob body or by the use of hard plastics. Further, it is desirable to provide positioning projections on each one of the implant blocks to prevent same from falling when inserted into a mold as an insert at the time of molding the knob body.

Furthermore, according to the present invention, there is also provided a method for manufacturing a manual control knob suitable for use on an endoscope for manipulation of an insertion instrument, the manual control knob being of the sort having a knob body of synthetic resin molding largely constituted by a ring-like top plate and a peripheral wall portion of a predetermined width formed integrally along marginal edges of the top plate, an aperture perforated centrally through the top plate, a plural number of lever portions projected radially outward from angularly spaced positions around outer periphery of the top plate, each one of the lever portions being provided with a finger grip surface at an outer distal end, and the aperture of the top plate being fitted on a rotating shaft projected from a manipulating head assembly of the endoscopic insertion instrument, the method comprising the steps of: preparing an insert member having a plural number of implant blocks at outer distal ends of radial connecting arms extending radially outward from a center core; setting the insert member within a cavity of a mold in a molding stage of the knob body, in such positions that the respective implant blocks of the insert member are located in lever portions to be formed; introducing a synthetic resin material into the mold to form the knob body on the insert member, having the implant blocks completely embedded in the lever portions of the knob body by a cover wall portion formed integrally with the knob body to cover lower side of the implant blocks remote from the top plate of the knob body; and cutting off at least radial connecting arm portions falling within boundaries of the aperture in the top plate.

The above and other objects, features and advantages of the present invention will become apparent from the following particular description, taken in conjunction with the accompanying drawings which show by way of example preferred embodiments of the invention. Needless to say, the present invention should not be construed as being limited to the particular forms which are shown in the drawings.

DESCRIPTION OF PREFERRED EMBODIMENTS

Hereafter, the present invention is described more particularly by way of its preferred embodiment shown in the accompanying drawings. The endoscope as well as the angle manipulation mechanism which appear in the following description is conventional in general construction and has no differences in particular from the counterpart in the prior art which is described hereinbefore. The knob construction according to the present invention is applied to an operating knob of an angle manipulation mechanism of an endoscope in the following description. Needless to say, the knob construction according to the present invention can also be applied similarly to a knob for raising the posture of an inserted tool or the like.

Figure 1:
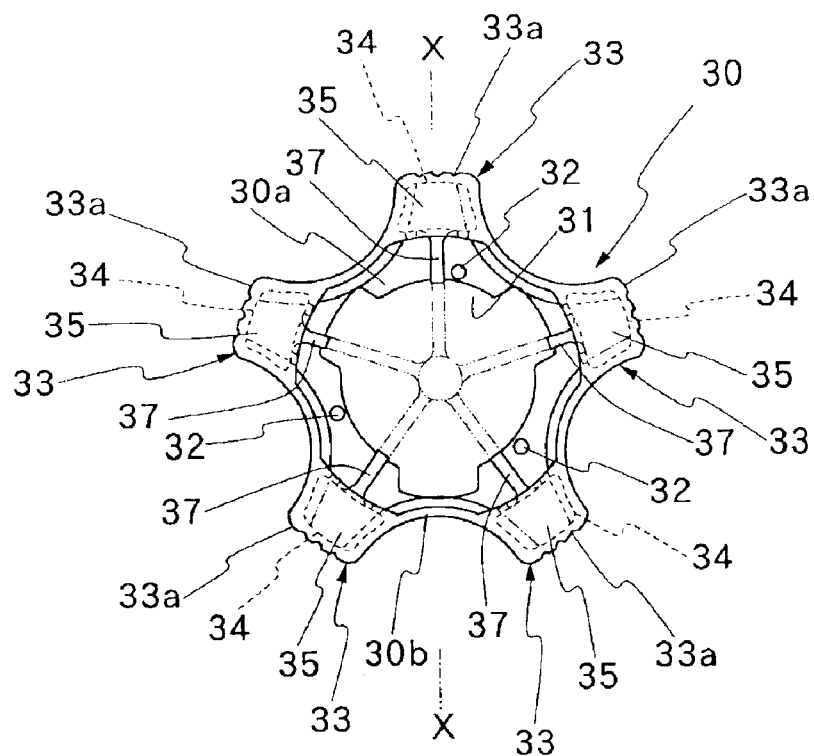
FIG. 1 is a schematic bottom view of a knob body embodying the present invention.
Figure 2:
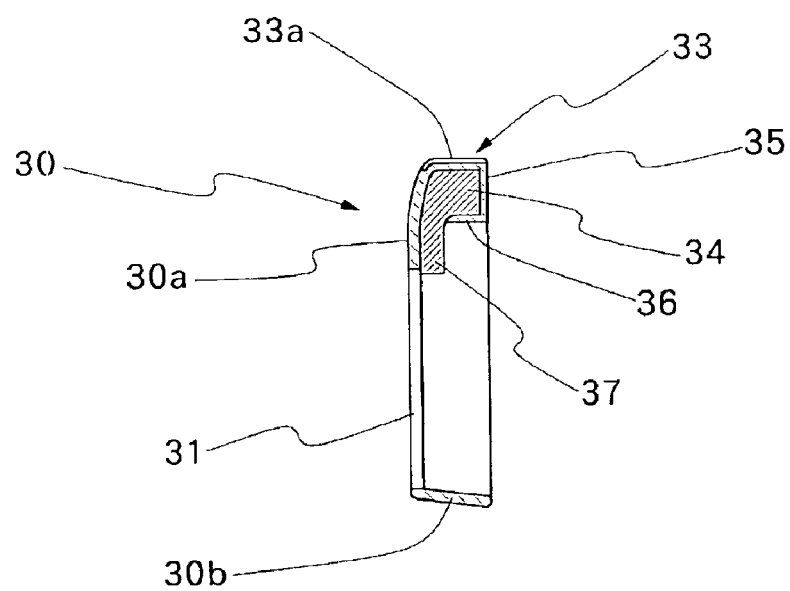
FIG. 2 is a schematic sectional view taken on line X—X in FIG. 1.
Figure 6:
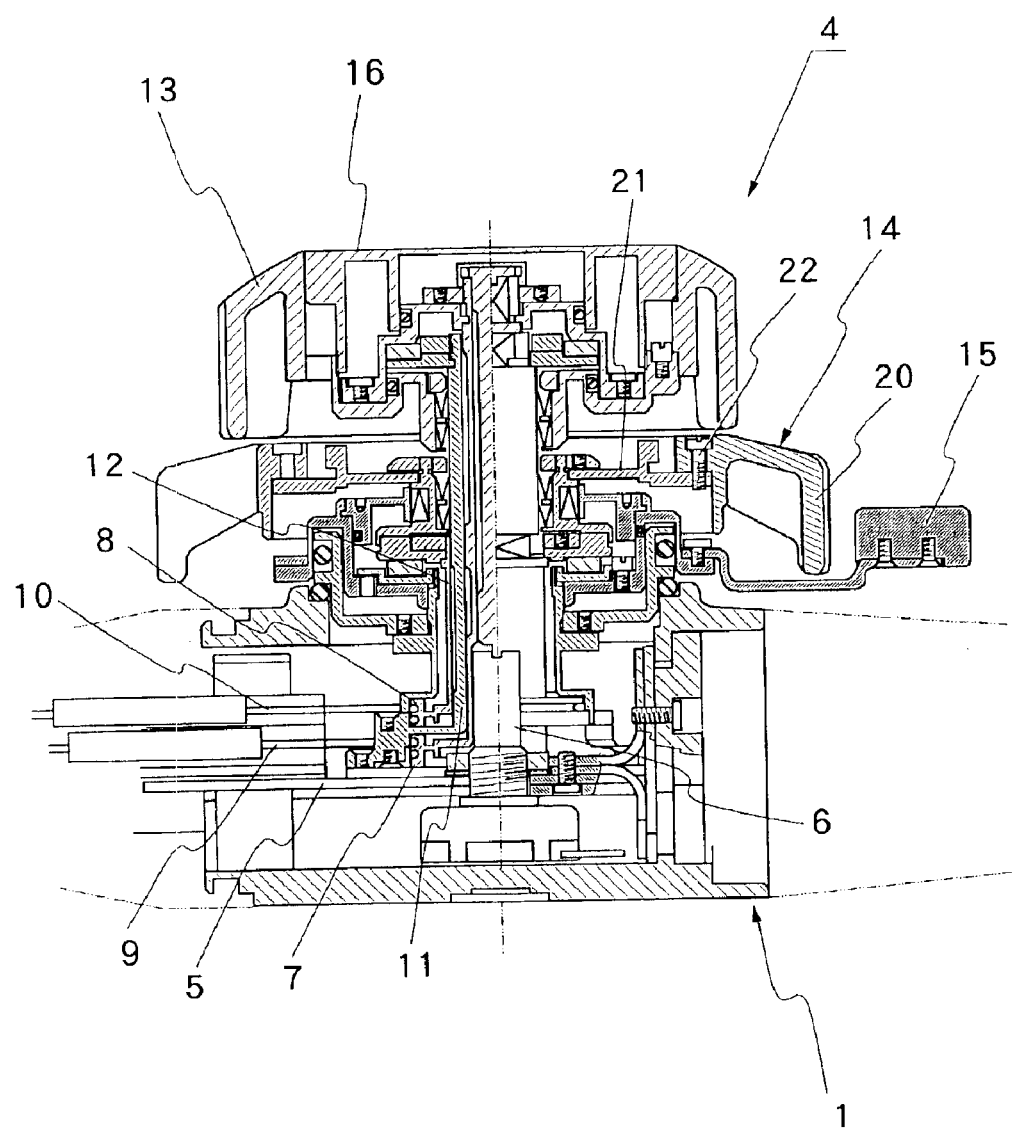
FIG. 6 is a schematic sectional view taken through an angle manipulation mechanism which is provided in the endoscope of FIG. 5.
Figure 7:
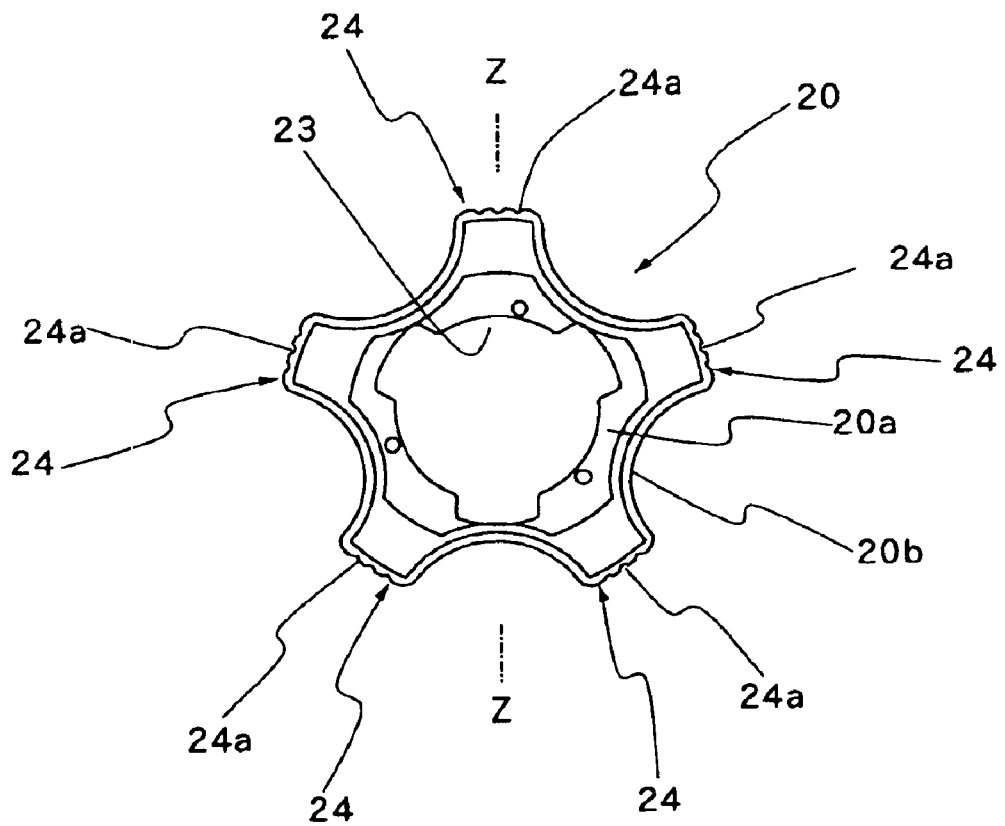
FIG. 7 is a schematic bottom view of a knob body by prior art.
Figure 8:
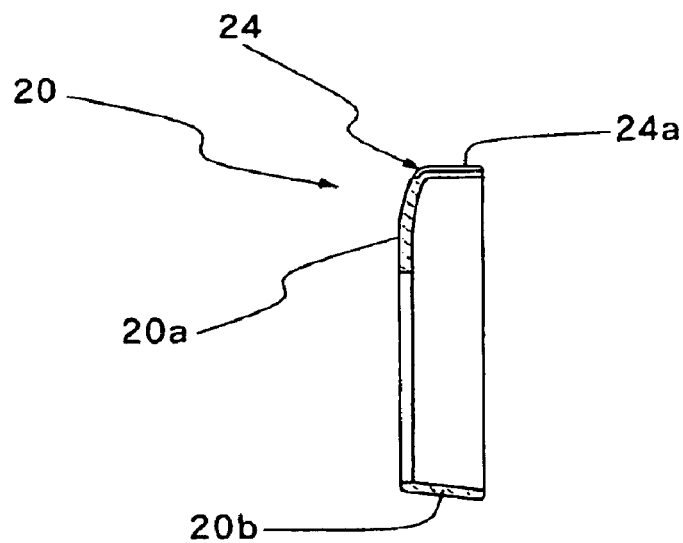
FIG. 8 is a schematic sectional view taken on line Z—Z of FIG. 7.

Shown in FIGS. 1 and 2 is the construction of a knob body according to the present invention. In these figures, indicated at 30a is a top plate portion and at 30b a circumventive side wall portion. The top plate portion 30a is provided with an aperture 31 in its center portion to receive a rotatable shaft therein as indicated as 12 in FIG. 6. Further, a plural number of screw receptacle holes 32 are provided in the vicinity of the aperture 31 in the top plate portion 30a to receive screw members which connect the top plate to a link member (a member equivalent to the link member indicated at 21 in FIG. 6) serving to fix the top plate member 30a to the rotatable shaft. The top plate portion 30a and the peripheral side wall portion 30b of the knob body 30 are integrally formed by synthetic resin molding. The knob body 30 is provided with a plural number of radially projecting lever portions 33 (e.g., five lever portions 33 in the particular embodiment shown) at angularly spaced positions, namely, at angular intervals around outer peripheries of the top plate portion 30a and the peripheral side wall portion 30b. At a projected distal end, each one of these lever portions 33 is provided with a finger grip surface 33a which has a sufficient breadth in both axial and circumferential directions. The width of each lever portion 33 is gradually increased in a radially inward direction or in a direction away from the finger grip surface 33a. Accordingly, the peripheral side wall portion 30b contains five arcuately indented portions at angularly spaced positions.

Figure 3:
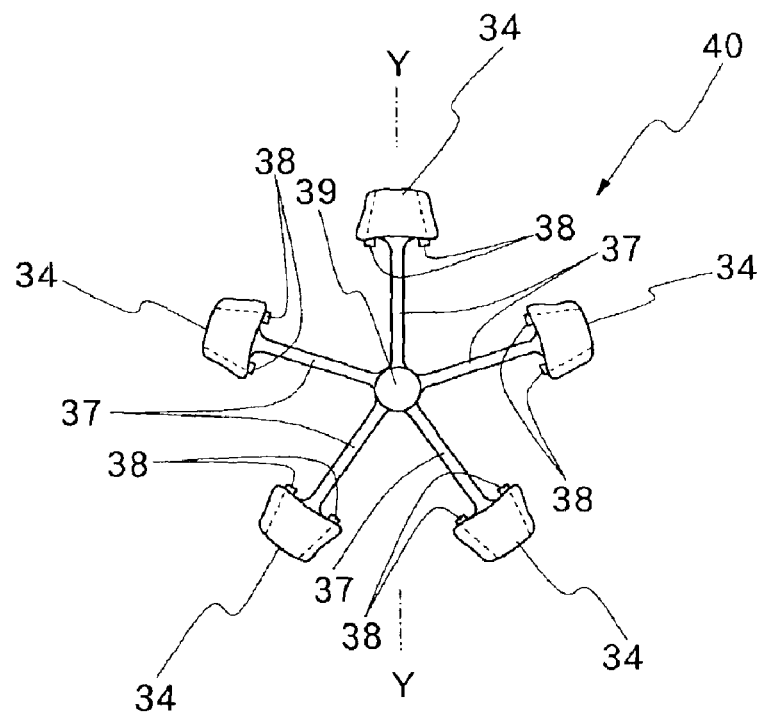
FIG. 3 is a schematic plan view of insert members.

An implant block 34 is embedded in each lever portion 33 to provide a substantially solid lever structure. On the side away from the top side which is joined with the top plate portion 30a, that is to say, on the lower side, the implant block 34 is completely covered with a cover wall portion 35 which is formed integrally with the peripheral side wall portion 30b. Furthermore, the part of a radially inner end face of the implant block 34 is covered in a hem portion which is formed integrally with the afore-mentioned cover portion 35. Extended out from the radially inner end face of each implant block 34 is a connecting arm 37 which is connected with other arms 37 from other implant blocks 34 at the center of the knob. Each one of the implant blocks 34 is provided with positioning projections 38 on an inner peripheral surface on the opposite sides of the connecting arm 37 as shown in FIG. 3 thereby to prevent the implant block 34 from being destabilized and caused to fall down under pressure of a supplied synthetic resin in an insert-molding stage which will be described hereinlater.

Figure 4:
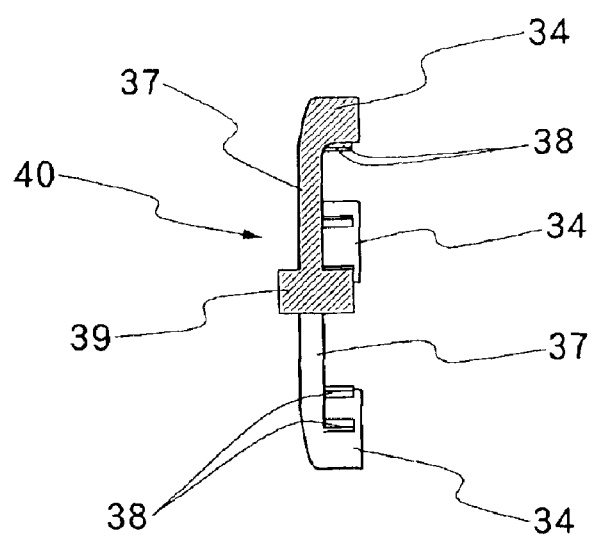
FIG. 4 is a schematic sectional view taken on line Y—Y of FIG. 3.

The implant blocks 34 which are completely embedded in the lever portions 33 of the knob body 30 as an insert at the time of molding the knob body 30. Shown in FIGS. 3 and 4 is an insert member 40 to be used in insert molding for embedding the respective implant blocks 34 in the lever portions 33 of the knob body 30.

The insert member 40 is composed of a core member 39, a plural number of connecting arms 37 which are extended radially outward from the core member 39 at angularly spaced positions, and implant block members 34 which are connected to outer distal ends of the connecting arms 37. As mentioned hereinbefore, each one of the implant blocks 34 is provided with positioning projections 38 on its inner peripheral surface which is connected to the arm 37. Both of the connecting arm 37 and positioning projections 38 are arranged to fall short of the lower end of the implant block 34 in vertical length. Therefore, the lower end of the implant block contains no projected portions over a predetermined width.

Described below is a method for molding the knob body 30 having the implant blocks 34 inserted therein. In the first place, the insert member 40 is prepared, for example, by synthetic resin injection molding. In this respect, shrinkage surface sinking may occur to the implant blocks 34 which form large masses on the insert member 40. However, existence of sunken surface spots on the implant blocks 34 gives rise to no problem because the implant blocks 34 are eventually completely embedded in lever portions of the knob.

The implant blocks 34 which are provided as functional parts on the insert member 40 are each connected to the core member 39 through the connecting arm 37. Therefore, the insert member 40 can be extremely easily set in a mold to be used for injection molding of the knob body 30. Besides, the core member 39 can be utilized as a registration means in positioning the insert member 40 within the mold. It follows that the insert member 40 can be easily set in position within the mold prior to molding the knob body 30.

The implant blocks 34 to be located in peripheral portions of the knob body 30 are each connected to an outer end of a long connecting arm 37, and are preferably formed in a minimum necessary thickness. This means that the implant blocks 34 can be caused to fall to one side or can be deviated in position under the influence of supplied resin pressure in the stage of molding in the insert member. However, the respective implant blocks 34 are restricted of movements and retained in position within a mold cavity in an extremely stabilized state thanks to the provision of the positioning projections 38 on the inner peripheral surfaces of the respective implant blocks 34.

The knob body 30 is formed by injection molding. Therefore, no matter whether or not the positioning projections 38 are provided on the insert member 40, it is desirable to select for the insert member 40 a material which has sufficiently high rigidity free of deformations under molding pressure. More preferably, the insert member 40 is formed of a material which is sufficiently high in rigidity and at the same time light in weight. On the other hand, the knob body 30 which is largely exposed to the outside should be formed of a material which has high resistance to chemicals. In this regard, examples of suitable material for the knob body 30 include noryl, polyether imide, polysulfone, polyphenylsulfone and the like. Further, the insert member should preferably have resistance to chemicals as well because it is exposed to the outside at least in part. Accordingly, usually the same material as the knob body 30 is selected fro the insert member 40. However, a different material may be selected arbitrarily for the insert member 40 as long as it has the required properties in resistance to chemicals, rigidity and lightness.

The insert member 40 is integrally molded into the knob body 30 at the time of molding the top plate portion 30 and the peripheral side wall portion 30b of the knob body 30. At this time, the cover portion 35 is formed integrally with the peripheral side wall portion 30b on the lower side of the implant blocks 34 (that side which is located away from the top plate portion 30a), and the inner enfolding wall portion 36 is formed integrally on the inner peripheral surface of the implant blocks 34. The lower cover wall portion 35 and the inner enfolding wall portion 36 are formed continuously from the peripheral side wall portion 30b of the knob body 30, and no boundary exists between these parts.

In this instance, the peripheral side wall portion 30b of the knob body 30, more particularly, the finger grip surface 33a on the lever portion 33 is preferably inclined to present an outwardly diverging shape in the downward direction, from the standpoint of enhanced maneuverability. The implant blocks 34 on the insert member 40 are preferred to be inclined in a similar shape so that the peripheral side wall portion 30b can be formed substantially in uniform thickness and its wall thickness can be reduced since it is held in intimate contact with the implant blocks 34.

Upon completion of the molding of the knob body 30 having the insert member 40 implanted therein, the molded knob structure is ejected from the mold and then the aperture 31 is opened in the top plate portion 30a by cutting and removing a corresponding part of the top plate 30a of the knob body 30. As a result, there is obtained a knob body 30 with substantially solid lever portions 33 each having an implant block in a completely embedded state.

Figure 5:
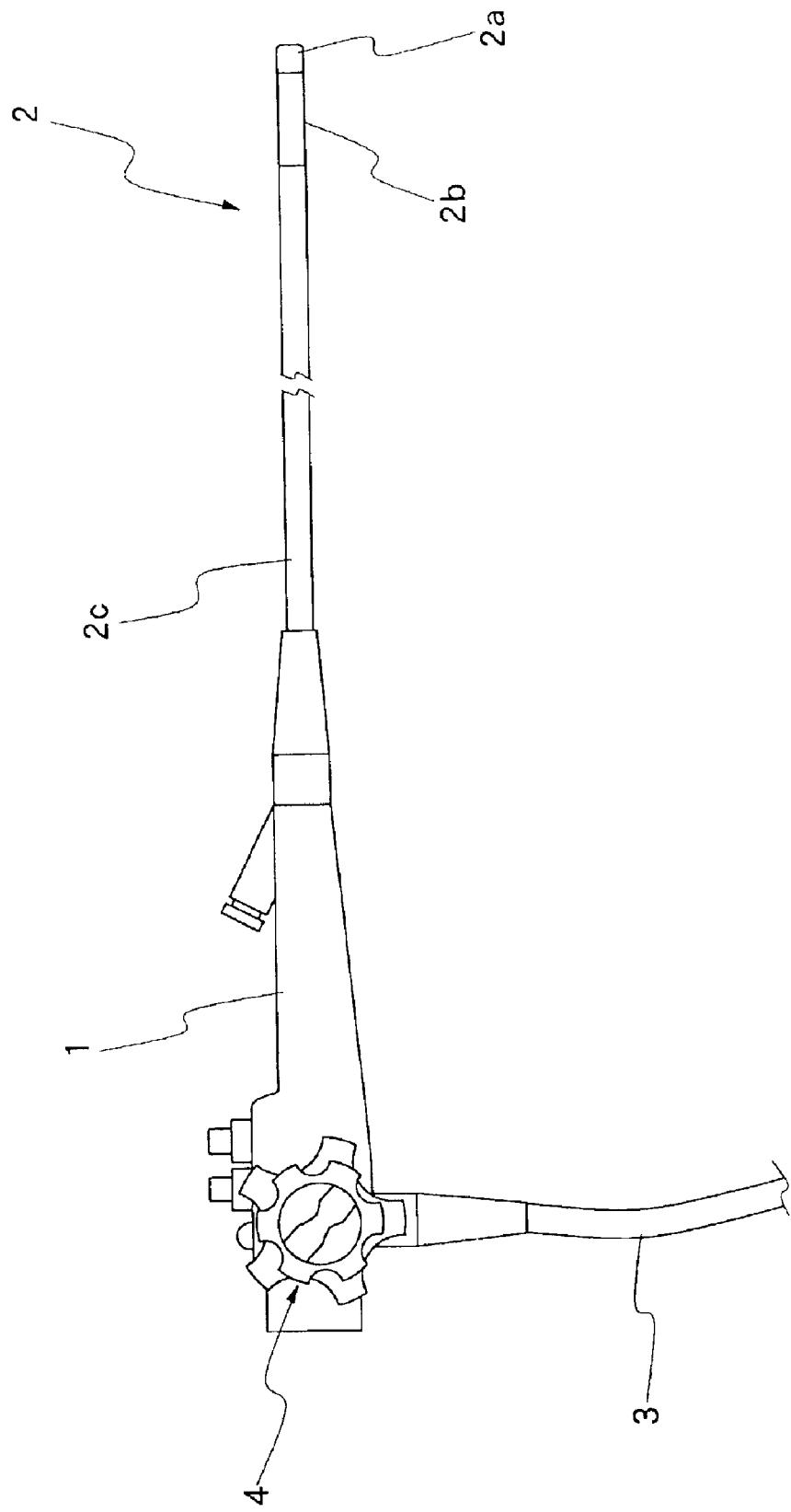
FIG. 5 is a schematic illustration showing the general layout of an endoscope.

The knob body 30, which is obtained by the insert molding as described above, is provided with substantially solid lever portions 33, and is satisfactory in surface accuracy because there is little possibilities of surface sinking occurring to the top plate portion 30a and the peripheral side wall portion 30b of the knob body 30 which are relatively small in wall thickness. In the endoscopic angle section manipulating mechanism as shown in FIG. 5, the knob body 30 can be connected to the rotatable shaft 12 through a link member to serve as a control knob 17. When an operator feels the necessity for bending the angle section of an endoscopic insertion instrument, the operator puts his or her fingers on the finger grip surfaces of the solid lever portions 33 of the knob body 30 for turning same. On such an occasion, the control knob 17 can be manipulated with better maneuverability, without experiencing a feeling of clumsiness.

When manipulated by an operator, the knob body 30 can be contaminated as a result. Contamination is most likely to occur on and in the vicinity of the finger grip surfaces 33a of the lever portions 33. In this instance, almost the entire outer surface of each lever portion 33 is constituted by the top plate portion 30a and the peripheral side wall portion 30b and at the same time by the back cover wall portion 35 and the enfolding wall portion 36 which are formed integrally with the top plate portion 30a and the peripheral wall portion 30b. That is to say, the surface of each lever portion 33 of the knob body 30 contains no seams, sunken spots or joint portions. Therefore, deposited contaminants can be easily removed from the knob body 30 by immersion in a cleaning liquid. In other words, the control knob of the endoscope is extremely favorable in terms of washability and disinfection factor. Although a stepped surface portion exists between the upper end of the enfolding wall portion 36 and a wall surface on the inner peripheral side of the implant block 34, there is little possibility of contaminants getting to and stagnating on the stepped surface portion which is located in a deep portion of the knob body 30.

Subsequent to the insertion molding, the connecting arms 37 of the insert member 40 are cut off except the arm portions which remain radially on the outer side of the aperture 31 in the top plate portion 30a of the knob body 30. Of course the connecting arms 37 may be cut off completely if desired. However, in case the arm portions radially on the outer side of the aperture 31 are left as reinforcing ribs, it become possible to further reduce the wall thickness of the top plate portion 30a of the knob body 30. In addition, in connecting the knob body 30 to the rotating shaft 12 through a link member, the portions of the arms 37 can be utilized as an anti-rotation mechanism which prevents relative rotational movements between the knob body 30 and the link member.

What is claimed for patent is:

1. An endoscopic manual control knob suitable for use on an endoscope for manipulation of an insertion instrument, said manual control knob being of the sort having a knob body of synthetic resin molding largely constituted by a ring-like top plate and a peripheral wall portion of a predetermined width formed integrally along marginal edges of said top plate, an aperture perforated centrally through said top plate, a plural number of lever portions projected radially outward from angularly spaced positions around outer periphery of said top plate, each one of said lever portions being provided with a finger grip surface at an outer distal end, and said aperture of said top plate being fitted on a rotating shaft projected from a manipulating head assembly of said endoscopic insertion instrument, characterized in that:

said knob body is constituted by a synthetic resin molding having said top plate and said peripheral side wall portion molded integrally with each other and having implant blocks embedded in said lever portions of said top plate by insertion molding;

said implant blocks are provided as an insert member having implant blocks connected to outer distal ends of connecting arms extending radially outward from a central core portion in the fashion of spokes; and cover wall portions are formed integrally with said knob body to enshroud said implant blocks completely on a lower back side of said knob body facing away from said top plate.

2. An endoscopic manual control knob as defined in claim 1, wherein said connecting arms are cut off at intermediate portions and remaining arm portions are left on said knob body to serve as reinforcing ribs.

3. An endoscopic manual control knob as defined in claim 1, wherein said knob body is molded by the use of a synthetic resin material selected from noryl, polyether imide, polysulfone, polyphenylsulfone.

4. An endoscopic manual control knob as defined in claim 1, wherein said knob is employed as a knob for manipulating an angle section of said endoscopic insertion instrument into a desired direction.

5. An endoscopic manual control knob suitable for use on an endoscope for manipulation of an insertion instrument, said manual control knob being of the sort having a knob body of synthetic resin molding largely constituted by a ring-like top plate and a peripheral wall portion of a predetermined width formed integrally along marginal edges of said top plate, an aperture perforated centrally through said top plate, a plural number of lever portions projected radially outward from angularly spaced positions around outer periphery of said top plate, each one of said lever portions being provided with a finger grip surface at an outer distal end, and said aperture of said top plate being fitted on a rotating shaft projected from a manipulating head assembly of said endoscopic insertion instrument, characterized in that:

said knob body is constituted by a synthetic resin molding having said top plate and said peripheral side wall portion molded integrally with each other and having implant blocks embedded in said lever portions of said top plate by insertion molding;

cover wall portions are formed integrally with said knob body to enshroud said implant blocks completely on a lower back side of said knob body facing away from said top plate; and an inner peripheral side of said implant blocks are at least partly covered by enfolding walls which are formed integrally with said cover wall portions.

6. An endoscopic manual control knob as defined in claim 5, wherein said implant blocks are formed of the same synthetic resin material as said knob body.

7. An endoscopic manual control knob as defined in claim 5, wherein said knob body is molded by the use of a synthetic resin material selected from noryl, polyether imide, polysulfone, polyphenylsulfone.

8. An endoscopic manual control knob as defined in claim 5, wherein said knob is employed as a knob for manipulating an angle section of said endoscopic insertion instrument into a desired direction.

9. An endoscopic manual control knob suitable for use on an endoscope for manipulation of an insertion instrument, said manual control knob being of the sort having a knob body of synthetic resin molding largely constituted by a ring-like top plate and a peripheral wall portion of a predetermined width formed integrally along marginal edges of said top plate, an aperture perforated centrally through said top plate, a plural number of lever portions projected radially outward from angularly spaced positions around outer periphery of said top plate, each one of said lever portions being provided with a finger grip surface at an outer distal end, and said aperture of said top plate being fitted on a rotating shaft projected from a manipulating head assembly of said endoscopic insertion instrument, characterized in that:

said knob body is constituted by a synthetic resin molding having said top plate and said peripheral side wall portion molded integrally with each other and having implant blocks embedded in said lever portions of said top plate by insertion molding;

cover wall portions are formed integrally with said knob body to enshroud said implant blocks completely on a lower back side of said knob body facing away from said top plate; and each one of said implant blocks is provided with positioning projections on inner peripheral side thereby to stop said implant blocks from falling at the time of said insertion molding.

10. An endoscopic manual control knob suitable for use on an endoscope for manipulation of an insertion instrument, said manual control knob being of the sort having a knob body of synthetic resin molding largely constituted by a ring-like top plate and a peripheral wall portion of a predetermined width formed integrally alone marginal edges of said top plate, an aperture perforated centrally through said top plate, a plural number of lever portions projected radially outward from angularly spaced positions around outer periphery of said top plate, each one of said lever portions being provided with a finger grip surface at an outer distal end, and said aperture of said top plate being fitted on a rotating shaft projected from a manipulating head assembly of said endoscopic insertion instrument, characterized in that:

said knob body is constituted by a synthetic resin molding having said top plate and said peripheral side wall portion molded integrally with each other and having implant blocks embedded in said lever portions of said top plate by insertion molding;

cover wall portions are formed integrally with said knob body to enshroud said implant blocks completely on a lower back side of said knob body facing away from said top plate; and said finger grip surface on each one of said lever portions is inclined to diverge radially outward in a direction away from said top plate of said knob body.

* * * * *